US010342530B2

(12) United States Patent
Halfon et al.

(10) Patent No.: US 10,342,530 B2
(45) Date of Patent: Jul. 9, 2019

(54) AMBIDEXTROUS SUPPORT BASE FOR A SUTURE THREAD

(71) Applicant: PETERS SURGICAL, Bobigny (FR)

(72) Inventors: Thomas Halfon, Gournay sur Marne (FR); Caroline Camedda, Groslay (FR)

(73) Assignee: PETERS SURGICAL, Bobigny (FR)

( * ) Notice: Subject to any disclaimer, the term of this patent is extended or adjusted under 35 U.S.C. 154(b) by 183 days.

(21) Appl. No.: 15/522,754

(22) PCT Filed: Oct. 29, 2015

(86) PCT No.: PCT/EP2015/075170
§ 371 (c)(1),
(2) Date: Aug. 3, 2017

(87) PCT Pub. No.: WO2016/066767
PCT Pub. Date: May 6, 2016

(65) Prior Publication Data
US 2018/0103949 A1   Apr. 19, 2018

(30) Foreign Application Priority Data

Oct. 29, 2014  (FR) ..................................... 14 60408
Feb. 25, 2015  (FR) ..................................... 15 51626

(51) Int. Cl.
*A61B 17/06* (2006.01)
*A61B 90/00* (2016.01)
*A61B 17/00* (2006.01)

(52) U.S. Cl.
CPC ........ *A61B 17/06133* (2013.01); *A61B 17/06* (2013.01); *A61B 17/06114* (2013.01);
(Continued)

(58) Field of Classification Search
CPC .............. A61B 17/06; A61B 17/06133; A61B 17/06114; A61B 17/06138;
(Continued)

(56) References Cited

U.S. PATENT DOCUMENTS 5,906,273 A     5/1999   Pohle et al.
2007/0227914 A1* 10/2007  Cerwin ............ A61B 17/06133
                                                 206/63.3
2007/0256945 A1  11/2007  Kennedy et al.

FOREIGN PATENT DOCUMENTS

EP    0082218    6/1983
EP    1106142    6/2001
EP    1275343    1/2003

OTHER PUBLICATIONS

Peters Surgical, "French Preliminary Search Report," FR Application No. 1460408 (dated May 18, 2015) (with English translation cover sheet).
(Continued)

*Primary Examiner* — King M Chu
(74) *Attorney, Agent, or Firm* — Womble Bond Dickinson (US) LLP

(57) ABSTRACT

The invention relates to a support base (1″) for a suture thread having two opposite sides (12, 14) and comprising on one side (12) thereof a storage channel (2) for a suture thread in a wound position, and a holding zone (4) of one end of the suture thread, the holding zone (4) being surrounded by the storage channel (2), the support base (1) being characterized by having a through-opening (5) between the two sides (12, 14) thereof, the through-opening (5) extending into the holding zone (4) and continuing from the holding zone (4) in such a way as to intersect the storage channel (2), and a shutter (8) moving between an open position for uncovering the through-opening (5) between the two sides (12, 14) thereof, and a closed position for at least partially opening
(Continued)

the through-opening (5), the moving shutter (8) being configured to project, in the open position thereof, from the side (14) of the base (1") which is opposite to the side (12) on which the storage channel (2) is formed.

17 Claims, 10 Drawing Sheets

(52) U.S. Cl.
CPC ............... *A61B 17/06138* (2013.01); *A61B 2017/00982* (2013.01); *A61B 2017/06147* (2013.01); *A61B 2090/0807* (2016.02)

(58) Field of Classification Search
CPC ........ A61B 17/00982; A61B 17/06147; A61B 2090/0807
USPC ....................................................... 206/63.3
See application file for complete search history.

(56) References Cited

OTHER PUBLICATIONS

Peters Surgical, "French Preliminary Search Report," FR Application No. 1551626 (dated Oct. 1, 2015) (with English translation cover sheet).
Peters Surgical, "International Search Report and Written Opinion," PCT Application No. PCT/EP2015/075170 (dated Jan. 26, 2016) (with English translation cover sheet).

\* cited by examiner

AMBIDEXTROUS SUPPORT BASE FOR A SUTURE THREAD

GENERAL FIELD

The invention relates to the field of surgical supplies packaging.

The invention relates more particularly to a portion of a packaging forming a support base for a suture thread.

PRIOR ART

Known in the state of the art are various types of packaging for suture thread.

A first type of packaging know for many years consists of a tearable or peelable sleeve or blister, which for its part can contain a second sleeve or blister which accommodates a support bobbin wherein the suture thread is wound. Bobbins are known that are formed from a simple cardboard core whereon the suture thread is wound circularly or in a 8-shape.

Also known are bobbins comprising a base having two opposite sides, the base comprising, on one of its sides, a storage channel for a suture thread in a wound position, and a holding zone for one end of the suture thread equipped with one or two needles, the holding zone being surrounded by the storage channel. The storage channel thus makes it possible to avoid the formation of knots. To extract the thread, an operator holds the bobbin with one hand, seizes with the other hand the end of this thread located in the holding zone using a needle holder, and thus unwinds the thread from the channel that contained it. By convention, it will be considered hereafter that holding the end of the suture thread means holding the needle when it is present, the needle being at the end of the suture thread.

However, the suture thread is accessible only from one of the two sides of the base. Consequently, the suture thread contained in such a bottom is not as easy to extract, depending on whether the operator seizes the end of the thread using the right hand or using the left hand.

To correct this problem it is proposed in document U.S. Pat. No. 5,906,273, as illustrated in the appended FIG. 1, a bobbin E which is intended to be ambidextrous comprising, in addition to the aforementioned features, a through window O between the two sides of the base, the window O being formed in the holding zone.

An operator can seize the end of the suture thread from either of the two sides of the base, using one of his hands or the other. In a first usage, the operator can in fact seize with a first hand (the right one for example) the end of the thread from the side on which the storage channel and the holding zone extend; and in a second alternative usage, the operator can seize the end of the thread located in the holding zone inserted from the opposite side of the base using his second hand (the left one here). The suture thread will then, during its extraction, pass through the through window, as illustrated in FIG. 2.

However, the motion according to this second usage is complex.

Moreover, during the extraction of the thread in this second usage, the suture thread is exposed to friction which is not encountered in the first usage. As the storage channel surrounds the through window, the thread, during extraction, stretches and forms an acute angle at an inner edge of the storage channel, which is a first source of friction, and possibly on an edge of the through window, second source of friction, at point P illustrated in FIG. 2. Such friction can not only damage the suture thread, with a generally small diameter, but also lead to resistance making extraction more difficult.

Also proposed, in document EP 1 106 142 A2 is a support base comprising a peripheral holding zone wherein in formed a through opening.

PRESENTATION OF THE INVENTION

The invention therefore aims to propose packaging for a suture thread from which the suture thread can be extracted as easily by the right hand as by the left hand, without risk of damaging or jamming the suture thread by one or the other of these usages.

To this end, a base support for a suture thread is proposed having two opposite sides and comprising, on one of its sides, a storage channel for a suture thread in a wound position, and a holding zone for an end of the suture thread, the holding zone being surrounded by the storage channel, the support base being characterized in that it has a through opening between its two sides, the through opening extending in the holding zone and continuing from the holding zone so as to intersect the storage channel. The support base also comprises a shutter movable between an open position for uncovering the through opening between its two sides, and a closed position for blocking at least a portion of the through opening, the movable shutter being configured to project, in its open position, from the side of the base opposite to the side on which the storage channel is formed.

When an operator causes the end of the suture thread to run through the through opening, and he pulls on this end so as to unwind the suture thread, this thread will naturally leave the portion of the opening located in the holding zone and extend along an axis having a slight angular deviation with respect to the thread winding trajectory in the storage channel, this deviation being impressed into the portion of the through opening which intersects the storage channel. The operator can thus, by moving his two hands apart from one another, unwind the thread without having the thread put under heavy mechanical loads by any edge of the through opening.

The invention can also be completed by the following characteristics, taken alone or in any one of their technically possible combinations.

The storage channel being delimited externally by a peripheral wall constituting a free edge of the base, the through opening can be continued until it also interrupts the peripheral wall. Such an extension of the through opening makes it possible to limit friction on the thread during extraction even when the operator moves his two hands away from one another during a natural circular-arc motion.

The storage channel can also comprise a first segment of which a first end leads into the through opening, the end of the thread located in the central holding zone leaving the storage channel through the first end. When the operator moves the end of the thread away from the base during extraction, the thread thus extends naturally between the first end of the segment and the end of the thread without complex prior handling.

The first segment can be rectilinear along a longitudinal axis, so as to offer the operator a preferred extraction axis wherein friction is minimized.

The first end can have a junction edge connecting the two sides of the base, the junction edge extending perpendicularly to the longitudinal axis. If, during extraction of the suture thread from the base, the operator carries out a natural circular-arc movement, the suture thread slides progressively along on the junction edge without catching.

The storage channel can also comprise a second segment of which a second end facing the first end also leads into the through opening, the second segment also extending along the same longitudinal axis. Thus, even if the through opening locally interrupts the storage channel between the first segment and the second segment, the suture thread is not deflected by the presence of this opening, and the unwinding of the thread can take place without additional friction.

The first end and the second end can also have the same widths between the holding zone and the peripheral wall of the base.

The through opening can extend between the two facing ends of the segment over a first length along the longitudinal axis, and extend in the holding zone over a second length parallel to and greater than the first length. This makes it possible to facilitate grasping of the end of the suture thread from the side opposite to that at which the holding zone is formed, while avoiding having the portions of the wound suture thread, accessible between the ends of the first segment and the second segment opposite one another, slide toward the holding zone, thus interfering with grasping the end of the suture thread.

The first segment can have a length along the longitudinal axis greater than that of the second segment. The first segment thus has a greater grasping surface for the operator, and makes it possible to thus increase comfort in extraction.

Moreover, the storage channel can have a substantially elliptical shape. Such a shape, with no acute angles, makes it possible to avoid friction inside the channel during unwinding of the suture thread and to minimize the shape memory of the thread once unwound.

The support base can also be made of a rigid material, easier to grasp than a simple cardboard core support, and/or impermeable to fluids, the manufacture whereof allows more varied geometries.

The support base can also comprise a stiffening rib projecting from at least one of the two opposite sides of the base, the stiffening rib extending along an edge of the through opening.

The stiffening rib can extend between the through opening and a segment of the storage channel having the overall shape of a C.

The movable shutter can have a connection end mounted pivotally on a portion of the base integral with the peripheral wall, and a free edge opposite to the connection end and positioned to be aligned with or extending beyond the peripheral wall when the movable shutter is positioned in its closed position. Such a free edge makes it possible to easily grasp the movable shutter to move it from its closed position toward its open position.

The movable shutter can have two opposite sides each forming a portion of the opposite sides of the base when the movable shutter is positioned in its closed position. Thus, the thickness of the support base remains small despite the addition of the movable shutter.

The invention also relates to a method for extracting a suture thread wound in the storage channel of a support base of the aforementioned type, the method comprising the following steps:
- insertion of a grasping means through the through opening by the side of the base opposite to the side on which the storage channel is formed,
- seizure of the end of the suture thread held in the holding zone by means of the grasping means passed through the through opening,
- mutual separation of the base and of the end of the suture thread seized by the grasping means.

In the event that the base comprises a movable shutter, the method above can include a step consisting of moving the movable shutter (8) from its closed position into its open position, before the insertion step.

DESCRIPTION OF THE FIGURES

Other features, aims and advantages of the invention will be revealed by the description that follows, which is purely illustrative and not limiting, and which must be read with reference to the appended drawings wherein.

In all the figures, similar elements have similar reference numbers.

DETAILED DESCRIPTION OF THE INVENTION

Figure 1:
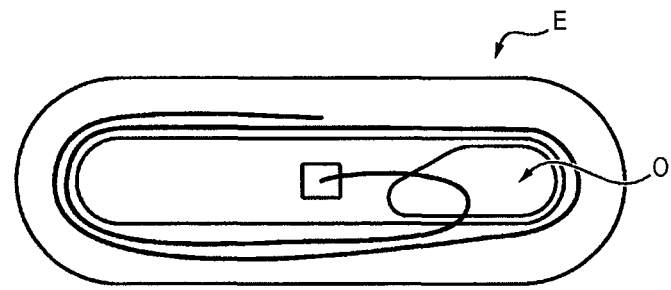
FIGS. 1 and 2, already discussed, show a known packaging for suture thread.
Figure 2:
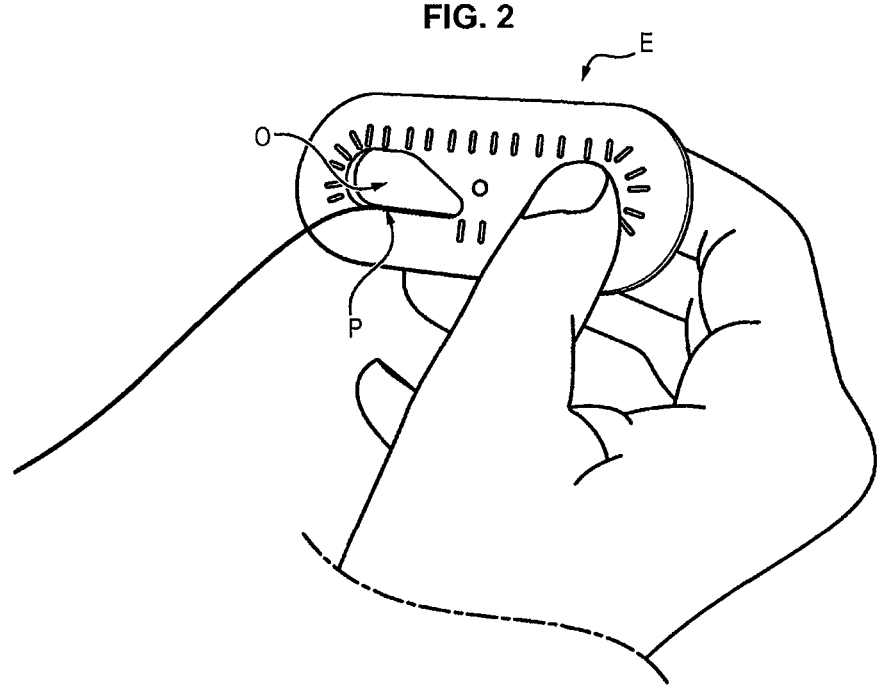

FIGS. 1 and 2 have already been described.

Packaging for suture thread comprises a blister pack or sleeve (not illustrated) and a substantially flat support base 1 designed to be inside the envelope.

Figure 3:
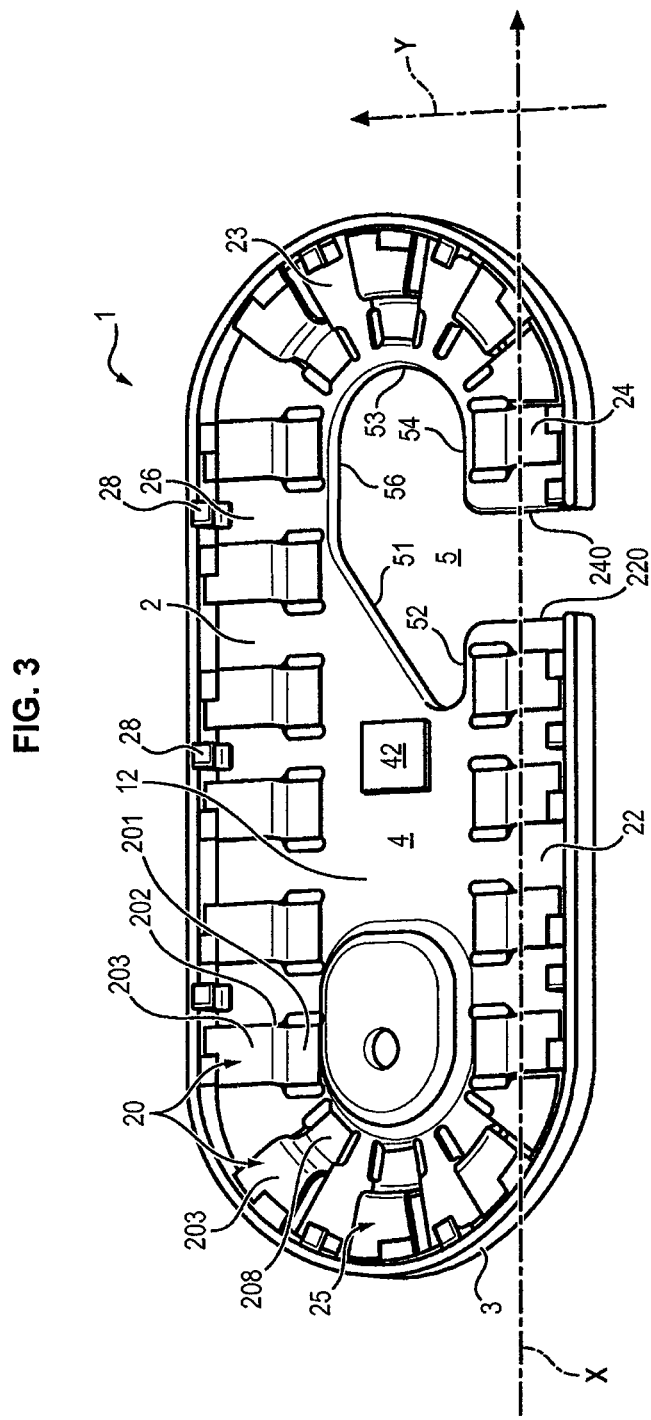
FIGS. 3 and 4 are two front views of a support base for a suture thread according to a first embodiment of the invention.
Figure 4:
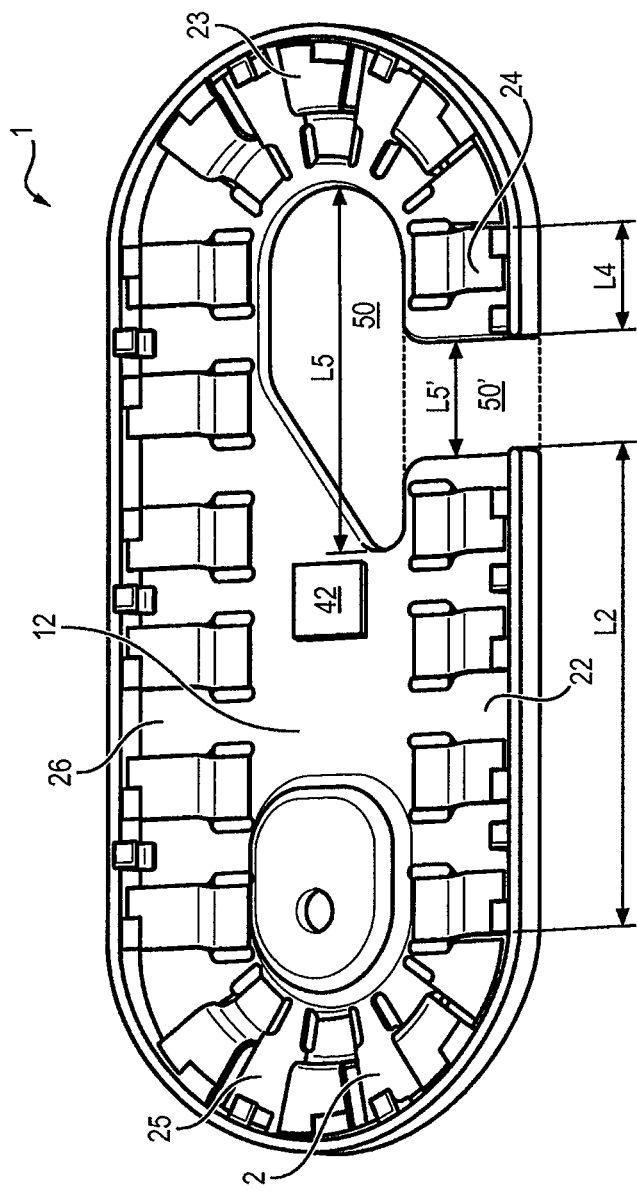
Figure 5:
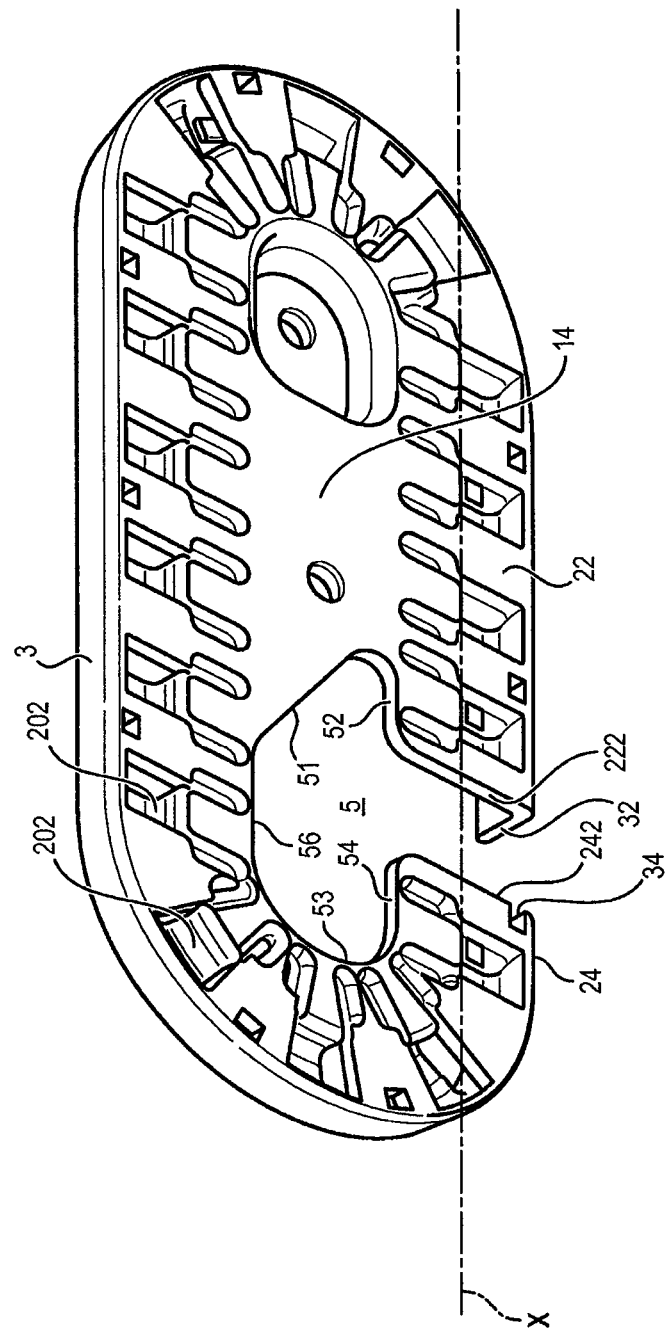
FIG. 5 is a back view of the support base already shown in FIGS. 2 and 3.

Referring to FIGS. 3 through 5, the support base 1 comprises a first side 12 and a second side 14 opposite to the first side 12.

The support base has a contour that is generally oval, elliptical or racetrack shaped.

The surface of the first side 12, visible in FIGS. 3 and 4, is divided into two zones: a central holding zone 4 and a peripheral zone surrounding the holding zone 4, a peripheral zone whereon is formed a storage channel 2 designed to contain a suture thread.

The storage channel 2 is defined by an exterior peripheral wall 3 and interior retention means, the wall and said retention means projecting from the first side 12.

The exterior wall 3 has an exterior surface forming a free edge of the base 1. This free edge is graspable by an operator.

The exterior retention means delimit the holding zone 4. In the embodiment illustrated in the figures, these retention means are formed by a plurality of fingers 20 projecting from the side 12 of the base 1. The fingers 20 are positioned along a racetrack shaped or oval trajectory circumscribed by the free edge of the base 1, with a similar trajectory. A suture thread can be accommodated in the storage channel 2 in a similar trajectory or at least an elliptical trajectory.

Each finger 20 has a flexible portion 201 integral with the base and extending in the plane of the base. The flexible portion 201 has a thickness suited to serve as an elastic pivot to the corresponding finger 20. The flexible portion 201 is continued by an intermediate portion 202 forming a bend with the flexible portion 201 so as to project from the first side 12, perpendicularly to the first side 12 for example. The intermediate portion 202 is for its part continued by a terminal portion 203 forming a bend with the intermediate portion 202 and extending as a cantilever toward the peripheral edge 3 in a plane parallel to the plane of the base, so as to store a suture thread accommodated between the exterior wall of the channel and the intermediate portion 202.

The side 14 of the base opposite the side 12 is visible in FIG. 5. The base has a plurality of peripheral holes between its two sides 12 and 14 accessible from the side 14. Each peripheral hole is provided between the peripheral edge of the base and the flexible portion 201 of a corresponding finger 20. Each terminal portion 203 overhangs the corresponding peripheral hole.

Each peripheral hole has dimension slightly greater than the terminal portion which overhangs it so as to allow removal of the part from the mold.

The base 1 also has a through opening 5 between its two opposite side 12 and 14. This through opening 5 has a portion 50 extending within the central holding zone 4. The portion 50 is continued by a portion 50' which extends into the peripheral zone so as to locally interrupt the storage channel 2 and intersect the winding trajectory of the channel 2.

Consequently, a suture thread wound in the storage channel 2 will be visible from each of the two sides 12 and 14 of the base at the portion 50' of the through opening 5.

The portion 50' of the through opening 5 also extends up to the outer wall 3 so as to interrupt it locally. The through opening thus forms a bay in the plane of the base, the bay being accessible from the free edge of the base formed by the exterior wall 3.

In the embodiment illustrated in FIGS. 3 through 5, the storage channel 2 comprises a first segment 22 and a second segment 24 each extending along the same longitudinal axis X, each segment 22, 24 terminating in a respective end 220, 240 of the channel 2 which leads directly into the through opening 5.

The storage channel 2 consists of successive consecutive segments from the end 220: the first rectilinear segment 22, a first curved segment 25 with a 180 degree turn, a third rectilinear segment 26 parallel to the first segment 22, then another curved segment 23 with a 180 degree turn, then finally the second segment 24 terminated by the end 240. The two curved segments 23 and 25 are symmetrical and located on either side of the holding zone 4.

The curved segments 23 and 25 have a C shape overall when the general shape of the base is racetrack-shaped. Other curved shapes for the curved segments can, however, be provided.

The two ends 220 and 240, separated by the portion 50' of the through opening 5, are opposite one another and centered on the same longitudinal axis X so as to allow the suture thread to be wound into the storage channel 2 on an elliptical trajectory, free of sudden deflections likely to wear the thread locally during its unwinding.

Each end 220, 240 has a respective junction edge 222, 242 connecting the two sides 12 and 14 of the base, and a respective exterior edge 32, 34 which also terminates the exterior wall 3. The exterior wall and the junction edge are for example coplanar, and the exterior edge forms a right-angle bend with respect to the junction edge. At each end 220, 240, the corresponding pair formed from a junction edge and an outer edge is thus shaped like an L.

Each junction edge 222, 242 is rectilinear, smooth and extending in the plane of the base along a transverse direction Y perpendicular to the direction of the longitudinal axis X, between the corresponding exterior edge and the holding zone 4.

The portion 50 of the through opening 50 which is located in the holding zone is delimited by a contour of which a first end terminates in the junction edge 220 and a second end terminates in the junction edge 240.

The contour of the portion 50 of the through opening 5 has successive consecutive portions from the junction edge 220 until the junction edge 240: a first receding edge 52 running along the first segment 22 in the holding zone 4 parallel to the longitudinal axis X, a diagonal connecting edge 51 connecting the first segment 22 to the segment designated 26, a rectilinear edge 56 running along the first segment 26, a curved edge 53 running along the curved segment 23, and a second receding edge 54 running along the second segment 24 in the holding zone 4 parallel to the longitudinal axis X.

The through opening 5 thus delimited occupies an end portion of the holding zone 4, this portion being closer to the curved segment 23 than to the curved segment 25 which is opposite it.

A needle support 42 is attached to the surface portion on the side 12 located in the holding zone 4, and more precisely between the connecting edge 51 and the curved segment 25. Such a support 42 generally takes the form of foam wherein a needle can be stuck and from which the needle can easily be withdrawn. The support 42 is positioned in the holding zone 4 so that a needle stuck into this support 42 can partially overhang the portion 50 of the through opening 5 (typically ⅓ of the needle). Thus, for a large needle, the support 42 can be moved away from the edge 51.

The diagonal connecting edge 51 extends rectilinearly in a direction crossing the longitudinal axis X, the diagonal connecting edge 51 moving away from the segment 26 from the edge 56 to the edge 52. This crossing direction forms an angle typically comprised between 20° and 60° with respect to the direction of the longitudinal axis, in the plane of the base 1.

Such an orientation is suited for curved needles with variable lengths, currently used as suture needles. An arched needle can in fact be stuck into the support 42 so as to be contained in a plane parallel to that of the base 1, and to overhang the portion 50 of the through opening 5, thus facilitating grasping it as will be seen later.

The support base 1 can also include means for attaching a cardboard tag above the side 12, the tag being able to including entries for example.

These attachment means comprise for example a plurality of pins 28 extending from the peripheral wall toward the holding zone 4, these pins being located at a slightly greater height than the height occupied by the upper face of the portion 203 of the of the storage fingers 20. A cardboard tag having dimensions suited to the interior circumference of the wall 3 can thus be clamped between the plurality of pins 28 and the plurality of fingers 20.

The holding zone 4 can also comprise a portion locally elevated with respect to the rest of the holding zone, this elevated portion being designed to serve as a support for the cardboard tag. This locally elevated portion also offers a grasping zone for a user.

Insertion of the Suture Thread into the Support Base

The previously described support base can contain different types of suture thread:
- a thread comprising a needle crimped to one of its two ends;
- a thread comprising two needles crimped to its two facing ends;
- a thread comprising a single needle at both of its ends forming a loop. In this case, the two ends of the thread meet at the needle; or
- one or more naked threads called "strands."

Hereafter, the example of a thread equipped with a needle crimped to one of its ends will be used. By convention, it will also be considered that the needle itself constitutes the end of the suture thread; thus it will be understood that grasping the end of the suture thread means grasping the needle.

The suture thread can be accommodated in the support base 1 in the following manner.

The side 14 of the base 1 is placed on a flat support having a plurality of pins extending so as that each pin is partially accommodated in a corresponding hole left at a finger 20.

By pressing the base 1 on the flat support, each pin exerts pressure on the terminal portion 203 of a finger 20. The fingers 20 rise simultaneously at their flexible portion 201 and 202. The storage channel 2 is then accessible from the side 12 on an oval trajectory forming a closed line delimited internally by the intermediate portions 202 of the different fingers 20.

The needle is stuck into the support 42 located in the holding zone 4 of the base 1.

Moreover, the suture thread is wound for one or more turns around the intermediate portions 202 of the plurality of fingers 20, beginning with the finger of the first segment 22 which is closest to the end 220.

When the base 1 is withdrawn from the support, after the thread has been wound, each finger 20 resumes, by elasticity, its rest position wherein its terminal portion 203 extends parallel to the plane of the base, thus retaining a portion of the wound thread.

The suture thread is then accommodated in the base 1. The storage channel 2 makes it possible to avoid the formation of knots likely to hinder its extraction from the base 1.

At this stage, the suture thread thus has a terminal portion (on the needle side) not contained in the storage channel 2. This unwound portion of the thread in fact avoids the first end 220 of the segment 22, extends into the holding zone by overhanging the through opening 5, and terminates with the needle partially stuck into the support 42.

Extraction of the Suture Thread from the Support Base

How the suture thread can be extracted from the support base 1 according to a first usage will not be described with reference to FIGS. 6 through 8.

An operator clamps the base 1 between the fingers of his right hand, so that the side 14 faces him. The thread and the needle are therefore not entirely visible. He can for example grasp the exterior wall at the segment 22 using the thumb, and this same external wall at segment 26 using the index finger.

The operator holds in his left hand a grasping instrument such as pliers. The operator then causes the jaws of the pliers to pass from the side 14 of the base 1 through the through opening 5 at its portion 50. By passing through the through opening 5, the jaws of the pliers penetrate into the holding zone 4 and seize the non-wound portion of the suture thread which overhangs the through opening 5 (using the needle, which offers a better hold than the thread itself).

The operator removes the needle from the foam support 42, then causes the needle thus seized to pass through the through opening 5 from the side 12 to the side 14. The needle then penetrates into the half-plane of the space defined by the side 14 of the base 1 facing the operator.

Figure 7:
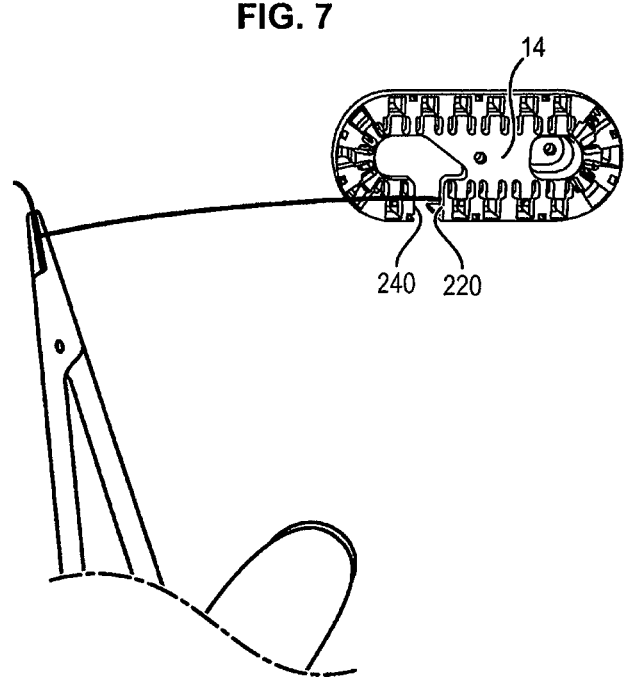

The operator then removes the pliers, generally called a "needle carrier," from the base 1 using the movement shown in FIG. 7. In doing this, the non-wound portion of the thread extends progressively between the first end 220 from which it is dispensed, and the jaws of the needle carrier, so that this portion of non-wound thread sweeps the junction edge 240 against the side 14 and describes a straight line substantially parallel to the longitudinal axis X of the first segment 22.

From the moment when the non-wound portion of the suture thread is correctly extended, the portion of the thread wound in the storage channel unwinds progressively, without any considerable deflection likely to cause friction and/or considerable crimping of the thread.

Figure 8:
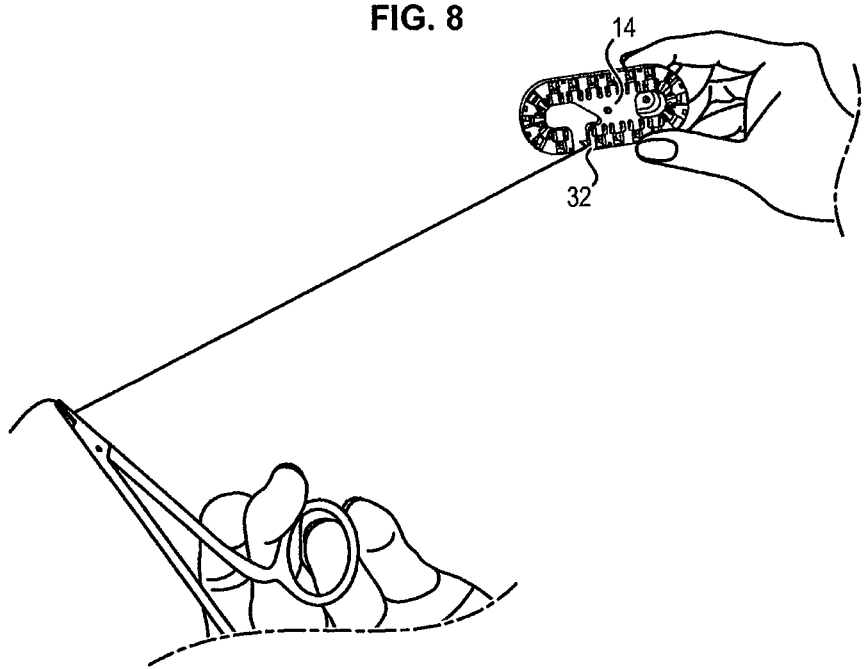

As the operator continues to separate both hands from one another, the grasped needle naturally follows a circular-arc trajectory, as shown in FIG. 8, and the wound thread unwinds. In this movement, the suture thread, while unwinding, when then run progressively along the junction edge 220 in the direction of the exterior edge 32 and until it touches the latter, without however imposing a considerable mechanical load on the thread. The thread then describes a relatively small angle, controllable by the operator, at this external edge 32 until the suture thread is entirely extracted from the base 1.

Figure 9:
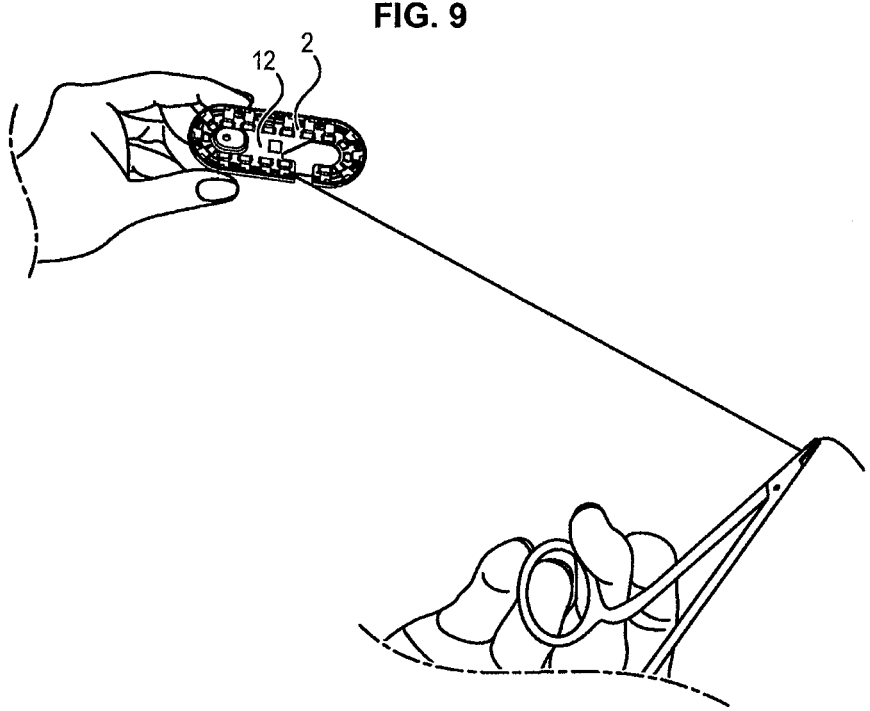
FIG. 9 represents the support base of FIG. 2, 3, 4 handled by an operator so as to extract the suture thread which it contains, according to a second usage.

According to a second alternative usage illustrated in FIG. 9, the operator seizes the packaging with his left hand, so that the side 12 to which the foam 42 is attached faces him. He can for example seize the exterior wall at segment 22 using the thumb, and the same exterior wall at segment 26 using the index finger.

Moreover, the operator seizes the pliers in his right hand. The needle is directly visible by the operator.

The operator seizes the needle stuck into the support 42 which faces him directly by means of the pliers.

By executing a movement similar to that described within the scope of the first usage described previously, the non-wound portion of the thread extends progressively between the first end 220 and the jaws of the pliers so that this non-wound portion of the thread is located in the half-plane of the space defined by the side 12 of the packaging, and describes a straight line substantially aligned with the axis X of the first segment (possibly sweeping the terminal portion of a finger 20 of the second segment 24 closest to the end 240).

As the operator continues to separate both of his hands from one another, the suture thread, during unwinding, with then approach, at the end 22, the exterior edge 32 until it touches the latter, without however imposing too great a mechanical load on the thread.

The operator desiring to extract the suture thread from the base 1 can then select the first or the second usage at his convenience, without having the thread subjected to additional friction in the first usage, with respect to the second usage.

The base 1 therefore defines an ambidextrous packaging part for a suture thread.

The length L2 of the segment 22 along the longitudinal axis X, from which the non-wound portion of the suture thread is dispensed, us preferably selected larger than the length L4 of the segment 24 so as to offer the operator a larger grasping surface on the base 1 and thus improve comfort in using the packaging to extract the suture thread that it contains. The length L2 of the segment 22 can for example be 2 to 5 times greater than the length L4 of the segment 24.

The portion 50 of the through opening 5 located in the holding zone 4 extends parallel to the longitudinal axis X over a maximum length L5, and the portion 50' of the through opening located between the two ends 220, 240 extends along the longitudinal axis X over a mean length L5' which is less than the length L5. Such a conformation makes it possible to have a relatively large through opening 5 in the holding zone, so as to facilitate access to the needle from the side 14 of the packaging, and relatively narrow between the two facing ends 220 and 240, which makes it possible to avoid having the wound portion(s) of the thread visible between the two ends be too long and therefore risking sliding into the holding zone, thus impeding access to the needle from the side 14 of the base 1.

The mean length L5 can for example be 2 to 4 times greater than the length L5'.

The length L5' of the through opening between the two ends 220 and 240 is preferably comprised between 5 mm and 20 mm, so as to allow extraction along a limited deflection axis while avoiding having the suture thread leaving the end 220 rubbing too strongly on the end 240 during extraction or on the cardboard tag when the latter is attached to the attachment means 28.

Moreover, it will be noted that having a rectilinear segment 22 from which the non-wound portion of the thread is dispensed makes it possible to naturally encourage a user concerned with not damaging the thread to carry out an extraction movement substantially along the corresponding longitudinal axis X.

The two junction edges 222 and 242 have the same widths in the transverse direction Y.

Moreover, the edges 32 and 34 of the exterior wall 3 at the facing ends 22 and 24 are also of the same height in a direction normal to the plane of the base 1.

It will also be noted that the rectilinear character of each junction edge 222, 242 facilitates the sliding of the suture thread while being extracted from the holding zone 4 toward the corresponding edge 32, 34.

The support base 1 is preferably made in a single piece, by molding for example.

The base 1 is preferably constituted by a rigid material allowing comfort in grasping it compared with cardboard, and/or impermeable to fluids so as to shorten drying during manufacture. The stiffness of this material is selected so as to allow the fingers to be raised without observing considerable residual deformation.

The base 1 can preferably have a maximum length (measured parallel to the longitudinal axis X) comprised between 70 and 200 mm, preferably 90 mm. The base 1 can also have a width (measured along the transverse axis Y) comprised between 30 and 70 mm, preferably 38 mm.

Figure 10:
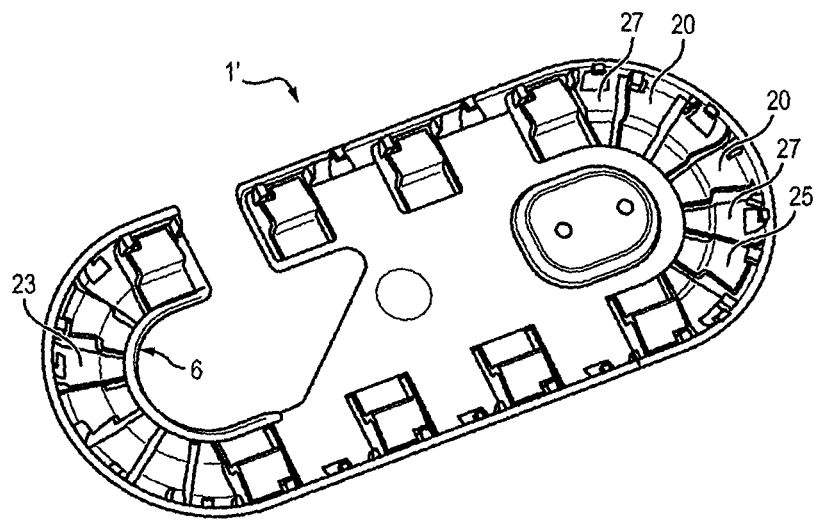
FIG. 10 is a front view of a support base for a suture thread according to a second embodiment of the invention.
Figure 11:
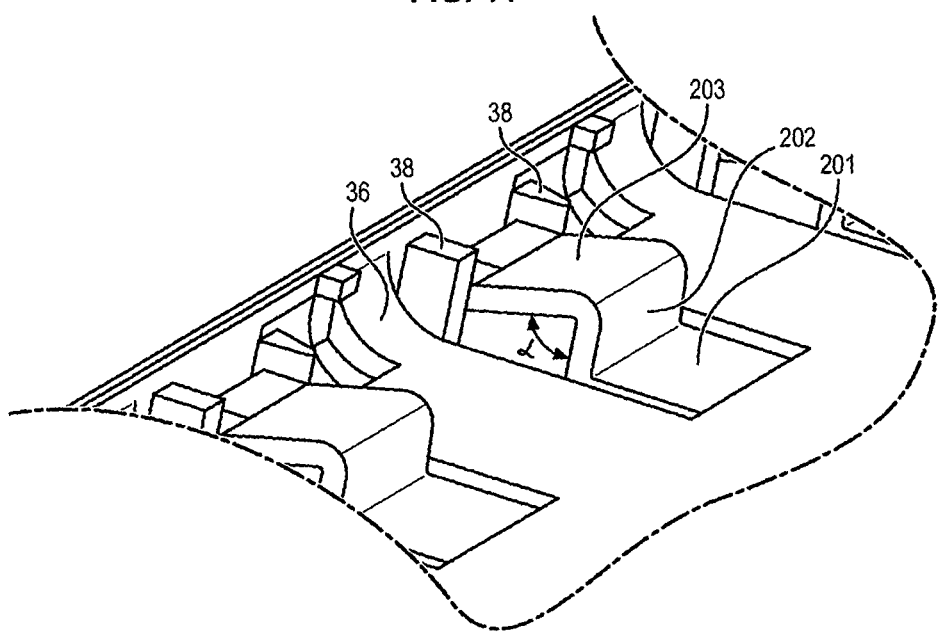
FIG. 11 is a partial three-quarters view of the embodiment of FIG. 10.
Figure 12:
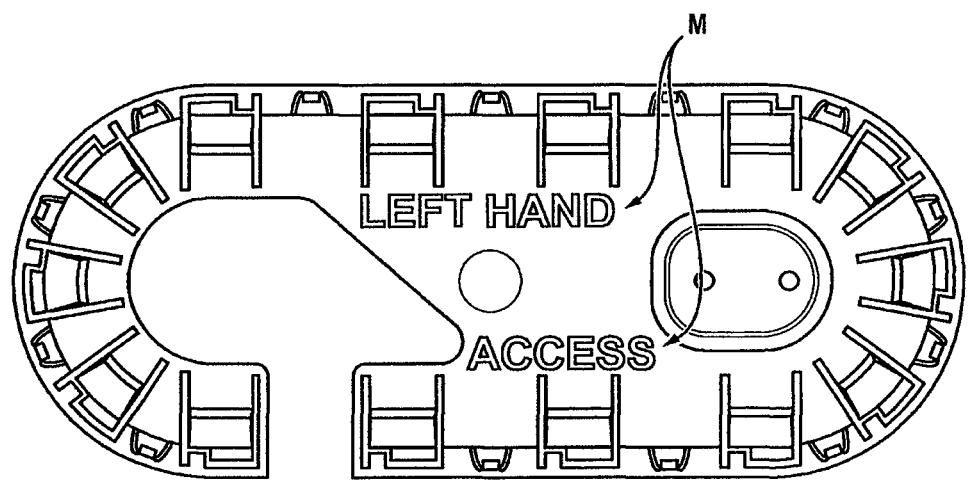
FIG. 12 is a back view of the support base show in FIGS. 10 and 11.

A second embodiment of the support base, designated 1' in FIGS. 10 through 12, comprises the following characteristics in addition to those of the base 1 already described.

Referring to FIG. 10, the internal storage means of the base 1' comprise, in addition to the storage fingers 20 already discussed, a plurality of ribs 27 projecting from the side 12, each rib 27 being located between two adjoining fingers 20 so as to complete the general trajectory already defined by the portions 202 of these fingers 20.

The ribs 27 are preferably located between the fingers defining the curved segments 23 and 25 so that the thread is not forced against the fingers 20 during its unwinding.

The base 1' also includes a stiffening rib 6 extending transversely on side 12, from the portion 53 defining an edge of the through opening 5. Such a rib 6 makes it possible to increase the stiffness of the segment 23 despite the presence of the opening 5, and also makes it possible to facilitate filling the mold used for the manufacture of the support base 1'.

The number of fingers can be reduced on the rectilinear segments 22, 24 and 26 with respect to the curved segments 23 and 25.

Referring to FIG. 11, the peripheral wall 3 of the base 1' has an internal surface leading into the storage channel 2 having a rounded profile with a progressive radius 36 with respect to the side 12.

In particular, the exterior edge 32 and the junction edge 222 do not form an "L," but rather form substantially a "C" due to this progressive radius 36 which interconnects the two edges 32 and 222. The pair of edges 34 and 242 has a similar structure.

In the base 1', the empty space left between the terminal portion of each finger 20 and the internal surface of the opposite peripheral wall 3 is enlarged with respect to the base 1 to facilitate injection during molding of the part. With such a modification, however, the fingers 20 have a tendency to hold the suture thread less.

Pins 38 are therefore provided projecting from the internal surface of the peripheral wall 3, transversely to the side 12 (and therefore transversely to the winding trajectory of the thread). These pins make it possible to separate the thread from the internal surface of the wall 3 and hence the empty space left above.

Each finger 20 of the base 1' comprises, like the base 1, the portions 201, 202 and 203. However, the terminal portion 203 does not extend parallel to the side 12 in the base 1', but rather at an angle. It is for example possible to provide an angle α between the intermediate portion 201 and the terminal portion 203 with a value comprised between 45° and 90°. This makes it possible to compensate for a residual deformation after raising the fingers 20 and increases the durability of the injection mold for manufacture of the base 1'.

Referring to FIG. 12, the side 14 comprises an entry M regarding manual preference. Here the entry is "left hand access" indicating that this side 14 offers the user better access if he is left-handed and he extracts the thread when this side 14 is facing him. This entry is for example formed by molding characters on the surface of the side 14, which offers a greater surface area for entries than the opposite side 12. An entry can also be written on the cardboard tag positioned above the side 12.

Figure 13:
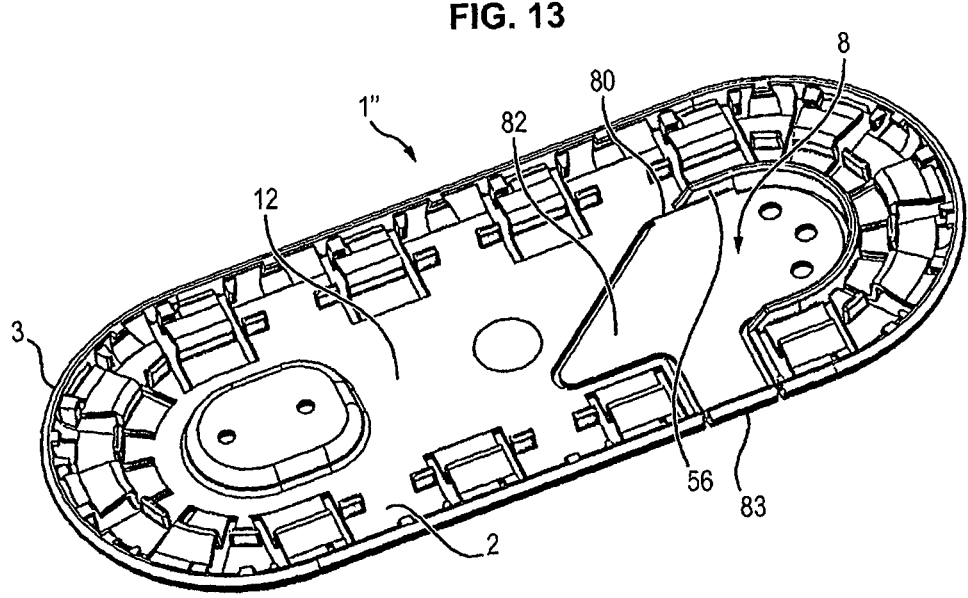
FIGS. 13, 14, 15 are views of a support base according to a third embodiment of the invention.
Figure 14:
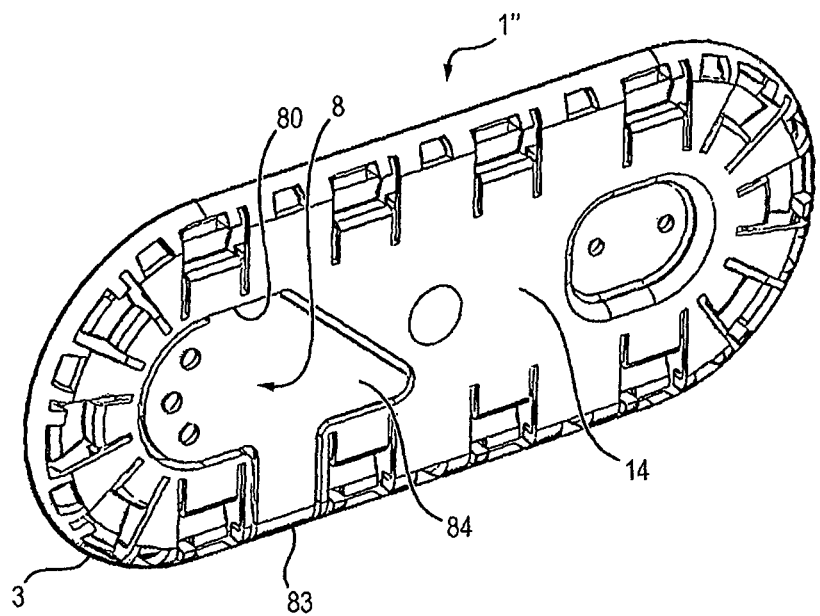
Figure 15:
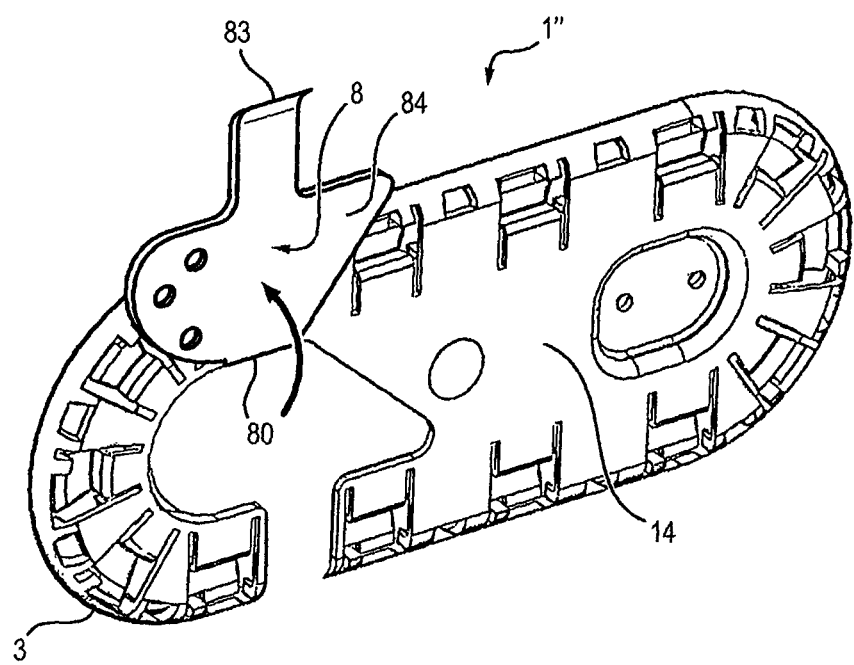

A third embodiment of the support base, designated 1", is illustrated in FIGS. 13 through 15.

The base 1" according to this third embodiment is distinguished from the two embodiments previously described by the fact that it also comprises a shutter 8 movable between an open position for uncovering the through opening 5 between its two sides 12 and 14, and a closed position for blocking at least in part the through opening 5.

The movable shutter 8 has a first side 82 forming a portion of the side 12 of the base 1", and a second side 84 opposite its first side 82 forming a portion of the side 14 of the base 1", when the movable shutter is positioned in its closed position.

The base 1" comprises hinge means for connecting the shutter 8 to the rest of the body of the base 1".

The hinge means comprise a connection end 80 of the movable shutter 8, this end being mounted pivotally to the rest of the body of the base 1". The rest of the body of the base 1" comprises in particular the peripheral wall 3 and the storage channel 2.

This end 80 defines a folding line with an axis parallel to the longitudinal axis X of the base 1".

The connecting end is for example connected to the rectilinear edge 56 of the through opening running along the segment 26 (this edge 56 is a free edge in the embodiments already described).

Moreover, the movable shutter 8 has a free edge 83, opposite to the connection end 80, which is positioned to be aligned with the peripheral wall 3 when the movable shutter 8 is positioned in its closed position. In other words, the free edge 83 of the shutter 8 completes the free edge formed by the peripheral wall 3, so as to define therewith a closed perimeter of the base 1" when the movable shutter 8 is positioned in its closed position.

In one variant of the movable shutter 8, the free edge 83 is not aligned with the peripheral wall 3, but extends beyond it toward the exterior of the base 1" with respect to the peripheral wall 3, in the plane defined by its two sides 12 and 14. This improves the ease of grasping the free edge 83 with a finger of a hand also holding the base 1" by another portion such as the peripheral wall 3.

In this manner, when the shutter 8 is moved into its open position by pivoting around the connection end 80, the portion 50' which extends in the peripheral zone so as to locally interrupt the storage channel 2 and intersect the winding trajectory of the channel 2 is completely uncovered.

The movable shutter 8 can moreover have a shape substantially complementary to the through opening 5, so as to completely block it when it is positioned in its closed position. A residual spacing can however be provided between the edges of the through opening 51, 52, 53, 54 and the movable shutter 8 in its closed position (spacing comprised between 0.5 and 3 millimeters, preferably 0.7 millimeters).

When it is complementary to the contour of the through opening 5, the shutter 8 includes a portion accommodated, in the closed rest position, in the portion 50' of the opening which extends in the peripheral zone so as to locally interrupt the storage channel 2 and intersect the winding trajectory of the channel 2. The connection end 80 is formed on the edge of the shutter 8 opposite to the edge of the shutter 8 which is flush with the exterior perimeter of the base 1", in the closed rest position.

The connection end 80 preferably made in one piece with the base 1" and the shutter 8, can be formed by local reduction in thickness with respect to the thickness of the base 1" and of the shutter 8. Such thinning facilitates the opening of the shutter 8 by folding at the connection 80.

Figure 6:
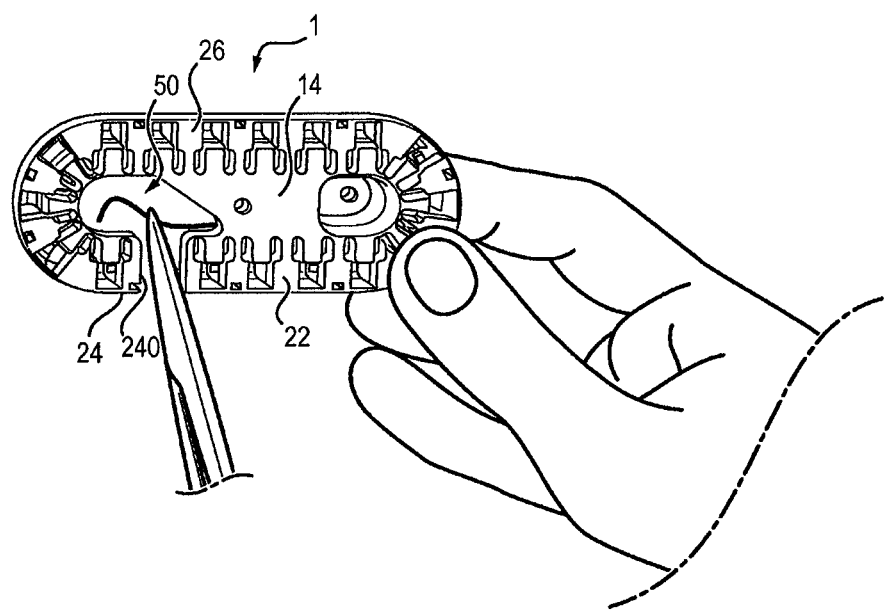
FIGS. 6, 7, 8 show the support base of FIG. 2, 3, 4 handled by an operator so as to extract the suture thread which it contains, according to a first usage.

When the shutter 8 is positioned in the open position, and operator can have access, by inserting a grasping instrument into the through opening 5 from the side 14 of the base 1", to the portion of the free end of the suture thread designed to be seized for its extraction, according to a usage similar to that described in relation with FIGS. 6 and 7.

When the shutter 8 is positioned in the closed position, the shutter 8 blocks the through opening 5. The shutter 8 then forms a protective screen between this end portion of the suture thread to be seized, located on the side 12 of the base, and any object located beyond the other side 14 of the base 1".

Such a shutter 8 makes it possible, in its closed position, to limit the free space of the suture thread designed to be seized for its extraction.

The shutter 8 is particularly advantageous when the free end of the suture thread to be seized is provided with a needle. In fact, the needle, which has a rigid structure, risks damaging the base 1" itself and/or a packing material wherein the base 1" is packaged, by friction or as a result of its detachment from its support 42, for example during transportation of the base 1".

The movable shutter 8 is positioned to project, in its open position, from the side 14 of the base opposite to the side 12 on which the storage channel 2 is formed, as shown in FIG. 15.

Preferably, the movable shutter 8 and the rest of the body of the base 1" form part of a single piece; the movable shutter 8 being then a portion formed in the same piece as the base 1", bendable from the base with respect to the rest of its body (particularly with respect to the storage channel 2 and to the holding zone 4).

Moreover, the movable shutter 8 can be configured so as to occupy its closed position at rest, and thus to be naturally driven by elastic springback toward this closed position, after having been moved by external loading toward the open position.

A suture thread wound in the base 1" can be extracted therefrom by means of the steps already described.

However, before passing a grasping instrument through the through opening according to the first usage already described in relation with FIGS. 6 through 8, a supplementary step is implemented consisting of uncovering the through opening by moving the shutter 8 into its open position, projecting from the side 14.

The operator can hold the shutter 8 in its open position using the hand that he is using for holding the body of the base during unwinding of the suture thread. The user can for example clamp the base by positioning his thumb against the side 14 in a position such that the thumb is partially located between the projecting shutter 8 and the through opening.

As a variant, the connection 80 is designed so that the movable shutter 8 can naturally remain in its open position, without external loading. This allows the operator seizing the base 1" to not have to manually hold the shutter 8 in the open position, and thus to improve comfort in grasping the base 1" for this operator.

The support base according to the invention is obviously not limited to the embodiments illustrated in the figures, but rather can be subjected to other variants of which a non-limiting list is given hereafter.

It is not obligatory for the through opening to intersect the storage channel over a complete section thereof, until reaching and interrupting the exterior wall 3, as was described in the embodiment illustrated. It is in fact sufficient for the through opening to continue from the holding zone so as to intersect at least partially a section of the storage channel, so as to allow limited deflection of the suture thread when the latter is withdrawn by the operator in one or the other of the two usages described.

The storage channel 2 can be modified to define a generally ellipsoidal winding trajectory, extending from a circular shape to a racetrack shape as shown in the embodiment illustrated.

The segments 22 and 24 can thus be curved and not rectilinear.

The storage channel 2 can be accomplished by means other than pivoting fingers 20. For example, the base 1 can consist of two parts forming, after assembly, the storage channel 2.

The non-wound portion of the suture thread can additionally leave segment 24 and not segment 22.

The facing ends 220 and 240 can have identical or different dimensions. For example, the junction edges 222 and 242 can have different respective widths.

The invention claimed is:

1. A support base (1") for a suture thread, the support base (1") having two opposite sides (12, 14) and comprising on one (12) of its sides:
 a storage channel (2) for a suture thread in a wound position,
 a holding zone (4) for an end of the suture thread, the holding zone (4) being surrounded by the storage channel (2),
the support base (1") being characterized in that it also comprises:
 a through opening (5) between its two sides (12, 14), the through opening (5) extending into the holding zone (4) and continuing from the holding zone (4) so as to intersect the storage channel (2),
 a shutter (8) movable between an open position for uncovering the through opening (5) between its two sides (12, 14) and a closed position for blocking, at least partially, the through opening (5), the movable shutter (8) being configured to project, in its open position, from the side (14) of the base (1") which is opposite to the side (12) on which the storage channel (2) is formed.

2. The support base (1") according to claim 1 wherein the storage channel (2) is delimited externally by a peripheral wall (3) constituting a free edge of the support base (1"), and the through opening (5) continues until it also intersects the peripheral wall (3).

3. The support base (1") according to claim 1, comprising a stiffening rib (6) projecting from at least one of the two opposite sides (12, 14), the stiffening rib (6) extending along an edge of the through opening (5).

4. The support base (1") according to claim 3, wherein the stiffening rib extends between the through opening (5) and a segment (23) of the storage channel (2) having the overall shape of a C.

5. The support base (1") according to claim 1, wherein the storage channel (2) comprises a first segment (22) of which a first end (220) leads into the through opening (5), the end of the thread located in the central holding zone leaving the storage channel (2) through the first end (220).

6. The support base (1") according to claim 5, wherein the first segment is rectilinear.

7. The support base (1") according to claim 5, wherein the first segment (22) extends along a longitudinal axis (X) and the first end (220) has a rectilinear junction edge (222) connecting the two sides of the base, the junction edge (222) extending perpendicularly to the longitudinal axis (X).

8. The support base (1") according to claim 5, wherein the storage channel (2) comprises a second segment (24) of which a second end (240) facing the first end (220) also leads into the through opening (5), the second segment extending along the same longitudinal axis (X).

9. The support base (1") according to claim 8, wherein the first end (220) and the second end (240) have the same length between the holding zone (4) and the peripheral wall (3) of the base.

10. The support base (1") according to claim 8, wherein the through opening (5) extends between the two facing ends of the segment (220, 240) over a first length (L5') along the longitudinal axis (X) and extends into the holding zone (4) over a second length (L5) parallel to and greater than the first length (L5').

11. The support base (1") according claim 5, wherein the first segment (22) has a length (L2) along the longitudinal axis (X) greater than that (L4) of the second segment (24).

12. The support base (1") according to claim 1, wherein the storage channel (2) has a shape suited to hold the suture thread wound along a substantially elliptical trajectory.

13. The support base (1") according to claim 1, made of a rigid and/or impermeable material.

14. The support base (1") according to claim 1, wherein the movable shutter (8) has a connection end (80) mounted pivotally on a portion of the base (1") integral with the peripheral wall (3), and a free edge (83) opposite to the connection end (80) positioned to be aligned with or extend beyond the peripheral wall (3) when the movable shutter (8) is positioned in its closed position.

15. The support base (1") according to claim 1, wherein the movable shutter (8) has two opposite sides (82, 84) each forming a portion of the opposite sides (12, 14) of the base (1") when the movable shutter is positioned in its closed position.

16. A method of extracting a suture thread from a support base (1"), wherein the support base has two opposite sides (12, 14) and comprises on one (12) of its sides:
 a storage channel (2) storing a suture thread in a wound position,
 a holding zone (4) for an end of the suture thread, the holding zone (4) being surrounded by the storage channel (2),
 a through opening (5) between its two sides (12, 14), the through opening (5) extending into the holding zone (4) and continuing from the holding zone (4) so as to intersect the storage channel (2),
 a shutter (8) movable between an open position for uncovering the through opening (5) between its two sides (12, 14) and a closed position for blocking, at least partially, the through opening (5), the movable shutter being configured to project, in its open position, from the side (14) of the base (1") which is opposite to the side (12) on which the storage channel (2) is formed,
wherein:
 inserting a grasping means through the through opening (5) by the side (14) of the base opposite to the side (12) on which the storage channel (2) is formed,
 seizing the end of the suture thread held in the holding zone (4) by means of the grasping means passed through the through opening,
 mutually separating the base (1") and the end of the suture thread seized by the grasping means.

17. The extraction method according to claim 16, further comprising moving the movable shutter (8) from its closed position into its open position, before inserting the grasping means through the through opening.

* * * * *